United States Patent
Carreras et al.

(10) Patent No.: US 7,407,941 B2
(45) Date of Patent: *Aug. 5, 2008

(54) N-DESMETHYL-N-SUBSTITUTED-11-DEOXYERYTHROMYCIN COMPOUNDS

(75) Inventors: Christopher Carreras, Belmont, CA (US); Yaoquan Liu, Castro Valley, CA (US)

(73) Assignee: Pfizer, Inc., New York, NY (US)

( * ) Notice: Subject to any disclaimer, the term of this patent is extended or adjusted under 35 U.S.C. 154(b) by 227 days.

This patent is subject to a terminal disclaimer.

(21) Appl. No.: 10/926,170

(22) Filed: Aug. 24, 2004

(65) Prior Publication Data

US 2005/0119195 A1    Jun. 2, 2005

Related U.S. Application Data

(60) Provisional application No. 60/498,108, filed on Aug. 26, 2003.

(51) Int. Cl.
*A61K 31/70*    (2006.01)
*C07H 17/08*    (2006.01)
(52) U.S. Cl. .......................................... 514/29; 536/7.2
(58) Field of Classification Search .................. 514/450, 514/29; 549/271; 536/7.2
See application file for complete search history.

(56) References Cited

U.S. PATENT DOCUMENTS

| | | | |
|---|---|---|---|
| 3,681,323 A | 8/1972 | Kurath et al. | |
| 3,681,325 A | 8/1972 | Freiberg | |
| 4,670,549 A * | 6/1987 | Morimoto et al. | 536/7.4 |
| 4,948,782 A | 8/1990 | Omura et al. | |
| 5,008,249 A | 4/1991 | Omura et al. | |
| 5,175,150 A | 12/1992 | Omura et al. | |
| 5,190,871 A | 3/1993 | Cox et al. | |
| 5,470,961 A | 11/1995 | Harada et al. | |
| 5,523,401 A | 6/1996 | Freiberg et al. | |
| 5,523,418 A | 6/1996 | Freiberg et al. | |
| 5,538,961 A | 7/1996 | Freiberg et al. | |
| 5,554,605 A | 9/1996 | Freiberg et al. | |
| 5,578,579 A | 11/1996 | Lartey et al. | |
| 5,654,411 A | 8/1997 | Lartey et al. | |
| 5,658,888 A | 8/1997 | Koga et al. | |
| 5,712,253 A | 1/1998 | Lartey et al. | |
| 5,824,513 A | 10/1998 | Katz et al. | |
| 5,830,750 A | 11/1998 | Khosla et al. | |
| 5,834,438 A | 11/1998 | Lartey et al. | |
| 5,854,407 A | 12/1998 | Harada et al. | |
| 5,922,849 A | 7/1999 | Premchandran et al. | |
| 5,959,088 A | 9/1999 | Miura et al. | |
| 6,077,943 A | 6/2000 | Omura et al. | |
| 6,084,079 A | 7/2000 | Keyes et al. | |
| 6,177,262 B1 | 1/2001 | Ziermann et al. | |
| 6,251,636 B1 | 6/2001 | Betlach et al. | |
| 6,303,767 B1 | 10/2001 | Betlach et al. | |
| 6,395,710 B1 | 5/2002 | Chu et al. | |
| 6,399,582 B1 | 6/2002 | Hlasta et al. | |
| 6,399,789 B1 | 6/2002 | Santi et al. | |
| 6,403,775 B1 | 6/2002 | McDaniel | |
| 6,451,768 B1 | 9/2002 | Chu | |
| 6,458,771 B1 | 10/2002 | Hlasta et al. | |
| 6,503,741 B1 | 1/2003 | Ashley et al. | |
| 6,514,944 B2 | 2/2003 | Chu | |
| 6,524,841 B1 | 2/2003 | McDaniel et al. | |
| 6,562,795 B2 * | 5/2003 | Ashley et al. | 514/29 |
| 6,590,083 B1 | 7/2003 | Hlasta et al. | |
| 6,750,205 B2 | 6/2004 | Ashley et al. | |
| 6,946,482 B2 * | 9/2005 | Santi et al. | 514/450 |
| 2002/0004229 A1 | 1/2002 | Santi et al. | |
| 2002/0025936 A1 | 2/2002 | Ashley et al. | |
| 2002/0094962 A1 | 7/2002 | Ashley et al. | |
| 2002/0192709 A1 | 12/2002 | Carreras et al. | |

FOREIGN PATENT DOCUMENTS

| | | |
|---|---|---|
| EP | 1314737 A1 | 5/2003 |
| GB | 1319216 | 6/1973 |
| JP | 60-218321 | 11/1985 |
| JP | 08-231580 | 9/1996 |
| WO | WO 00/01827 A2 | 1/2000 |
| WO | WO 01/60833 A2 | 8/2001 |
| WO | WO 03/090679 A2 | 11/2003 |
| WO | WO 2004/013153 A2 | 2/2004 |

OTHER PUBLICATIONS

Burger's Medicinal Chemistry and Drug Discovery, 5th edition, vol. I, Manfred E. Wolff, 1995, pp. 975-977.*
Modern Pharmacuetics, 3rd edition, Banker et al., 1995, pp. 596.*
U.S. Appl. No. 10/648,946, filed Aug. 26, 2003, Santi et al.

(Continued)

*Primary Examiner*—Elli Peselev
(74) *Attorney, Agent, or Firm*—Foley & Lardner LLP

(57) ABSTRACT

Compounds having the structure of formula I

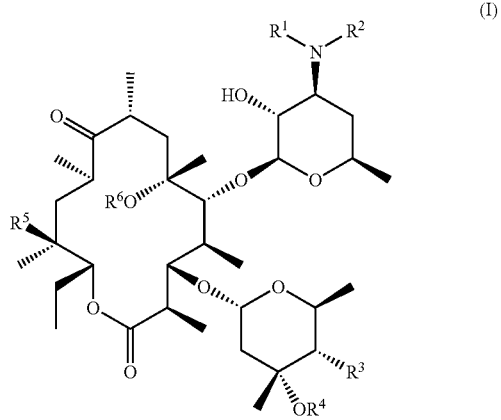

wherein $R^1$, $R^2$, $R^3$, $R^4$, $R^5$, and $R^6$ are as defined herein, are prokinetic agents and can be used to treat disorders of gastric motility.

4 Claims, No Drawings

OTHER PUBLICATIONS

U.S. Appl. No. 10/925,709, filed Aug. 24, 2004, Carreras et al.
Carreras et al., *Anal. Biochem.*, 300, 146-151 (2002), "Stable Expression of a Synthetic Gene for the Human Motilin Receptor: Use in an Aequorin-based Receptor Activation Assay".
Carreras et al., *J. Biotechnol.*, 92, 217-228 (2002), "*Saccharopolyspora erythraea*-catalyzed bioconversion of 6-deoxyerythronolide B analogs for production of novel erythromycins".
Chemical Abstracts No. 104:82047 (abstract of JP 60-218321).
Chemical Abstracts No. 125:329280 (abstract of JP 08-231580).
Cowles et al., *J. Pharmacol. Exp. Therapeutics*, 293 (3), 1106-1111 (2000).
Depoortere et al., *J. Gastrointestinal Motility*, 1, 150-159 (1989), "Structure-Activity Relation of Erythromycin-Related Macrolides in Inducing Contractions and in Displacing Bound Motilin in Rabbit Duodenum".
Faghih et al., *Biorg. & Med. Chem. Lett.*, 8, 805-810 (1998), "Preparation of 9-Deoxo-4"-deoxy-6,9-epoxyerythromycin Lactams 'Motilactides': Potent and Orally Active Prokinetic Agents".
Faghih et al., *Drugs Future*, 23 (8), 861-872 (1998), "Motilides and motilactides: design and development of motilin receptor agonists as a new class of gastrointestinal prokinetic drugs".
Faghih et al., *J. Med. Chem.* 41, 3402-3408 (1998), "Synthesis of 9-Deoxo-4"-deoxy-6,9-epoxyerythromycin Derivatives: Novel and Acid-Stable Motilides".
Faghih et al., *Synlett* 751 (Jul. 1998), "Entry into Erythromycin Lactams: Synthesis of Erythromycin A Lactam Enol Ether as a Potential Gastrointestinal Prokinetic Agent".
Frykman et al., *Biotechnol. Bioeng.*, 76, 303-310 (2001) "Precursor-Directed Production of Erythromycin Analogs by *Saccharopolyspora erythraea*".
Hauske et al., *J. Org. Chem.*, 47, 1595-1596 (1982), "Synthesis of 10,11-Anhydroerythromycin".
Hauske et al., *J. Org. Chem.*, 49, 712-714 (1984), "Regiospecific Synthesis of 9-Desoxoerythromycin A".
Khiat et al., *J. Peptide Res.* 52, 321-328 (1998), "Identification of the Motilide Pharamacophores Using Quantitative Structure Activity Relationships".
Lartey et al., *J. Antibiotics*, 48 (7), 730-732 (1995), "Stereoselective Deoxygenation of Erythromycin A at C12: Effect of Structure and Conformation on Prokinetic Activity".
Lartey et al., *J. Med. Chem.*, 38 (10), 1793-1798 (1995), "Synthesis of 4"-Deoxy Motilides: Identification of a Potent and Orally Active Prokinetic Drug Candidate".
Omura et al., *J. Antibiotics* 38, 1631-2 (1985), "Gastrointestinal Motor-Stimulating Activity of Macrolide Antibiotics and the Structure-Activity Relationship".
Rodriguez et al., *J. Ind. Microbio. Biotechnol.*, 8, 480-8 (2003), "Rapid Engineering of Polyketide Overproduction by Gene Transfer to Industrially Optimized Strains".
Steinmetz et al., *J. Med. Chem.*, 45, 4899-4902 (2002), "Structure of Erythromycin Enol Ether as a Model for Its Activity as a Motilide".
Sunazuka et al., *Chem. Pharm. Bull.*, 37 (10), 2701-2709 (1989), "Motilides, Macrolides with Gastrointestinal Motor Stimulating activity. II. Quaternary N-Substituted Derivatives of 8,9-Anhydroerythrmycin A 6,9-Hemiacetal and 9,9-dihydroerythromycin A 6,9-Epoxide".
Tsuzuki et al., *Chem. Pharm. Bull.*, 37 (10), 2687-2700 (1989), "Motilides, Macrolides with Gastrointestinal Motor Stimulating activity. I. O-Substituted and Tertiary N-Substituted Derivatives of 8,9-Anhydroerythromycin A 6,9-Hemiacetal".
Wermuth, "Designing Prodrugs and Bioprecursors," in Wermuth, ed., *The Practice of Medicinal Chemistry*, 2nd Ed., pp. 561-586 (Academic Press 2003).
Xue et al., *Proc. Natl. Acad. Sci. U.S.A.*, 96, 11740-11745 (1999), "A multiplasmid approach to preparing large libraries of polyketides".
Bierman et al., *Gene* 116, 43-49 (1992), "Plasmid cloning vectors for the conjugal transfer of DNA from *Escherichia coli* to *Streptomyces* spp."

* cited by examiner

N-DESMETHYL-N-SUBSTITUTED-11-DEOXYERYTHROMYCIN COMPOUNDS

CROSS-REFERENCE TO RELATED APPLICATIONS

This application claims the benefit of U.S. Provisional Application No. 60/498,108, filed Aug. 26, 2003, the disclosure of which is incorporated herein by reference.

BACKGROUND OF THE INVENTION

1. Field of the Invention

This invention relates to erythromycin analogs, methods of making them, and their use as prokinetic agents.

2. Description of Related Art

Gastrointestinal ("GI") motility regulates the orderly movement of ingested material through the gut to ensure adequate absorption of nutrients, electrolytes, and fluids. Proper transit of the GI contents through the esophagus, stomach, small intestine, and colon depends on regional control of intraluminal pressure and several sphincters, which regulate their forward movement and prevent back-flow. The normal GI motility pattern may be impaired by a variety of circumstances, including disease and surgery.

GI motility disorders include gastroparesis and gastroesophageal reflux disease ("GERD"). Gastroparesis, whose symptoms include stomach upset, heartburn, nausea, and vomiting, is the delayed emptying of stomach contents. GERD refers to the varied clinical manifestations of the reflux of stomach and duodenal contents into the esophagus. The most common symptoms are heartburn and dysphasia, with blood loss from esophageal erosion also known to occur. Other examples of GI disorders in which impaired GI motility is implicated include anorexia, gall bladder stasis, postoperative paralytic ileus, scleroderma, intestinal pseudoobstruction, irritable bowel syndrome, gastritis, emesis, and chronic constipation (colonic inertia).

Motilin is a 22-amino acid peptide hormone secreted by endocrine cells in the intestinal mucosa. Its binding to the motilin receptor in the GI tract stimulates GI motility. The administration of therapeutic agents that act as motilin receptor agonists ("prokinetic agents") has been proposed as a treatment for GI disorders.

The erythromycins are a family of macrolide antibiotics made by the fermentation of the Actinomycetes *Saccharopolyspora erythraea* (formerly *Streptomyces erythreus*). Erythromycin A, a commonly used antibiotic, is the most abundant and important member of the family.

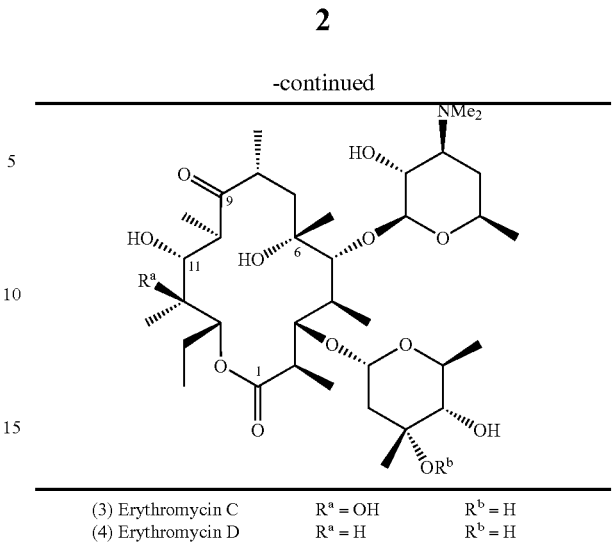

|   |   |   |
|---|---|---|
| (3) Erythromycin C | $R^a$ = OH | $R^b$ = H |
| (4) Erythromycin D | $R^a$ = H | $R^b$ = H |

The side effects of erythromycin A include nausea, vomiting, and abdominal discomfort. These effects have been traced to motilin receptor agonist activity in erythromycin A (1) and, more so, its initial acid-catalyzed degradation product (5). (However, the secondary degradation product, spiroketal (6), is inactive.)

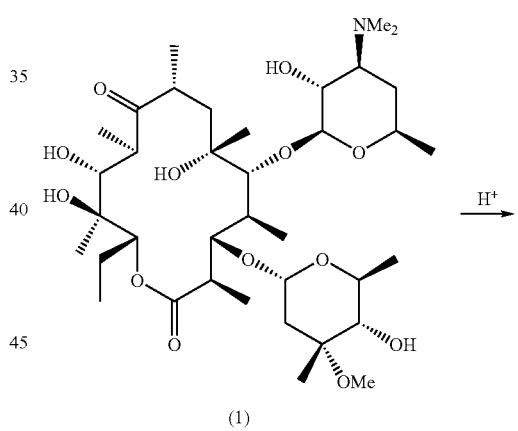

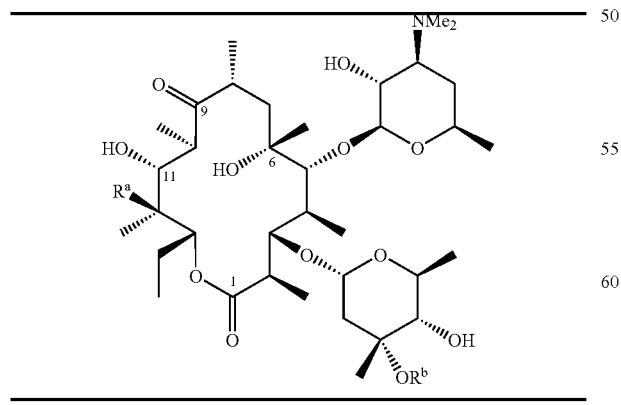

|   |   |   |
|---|---|---|
| (1) Erythromycin A | $R^a$ = OH | $R^b$ = Me |
| (2) Erythromycin B | $R^a$ = H  | $R^b$ = Me |

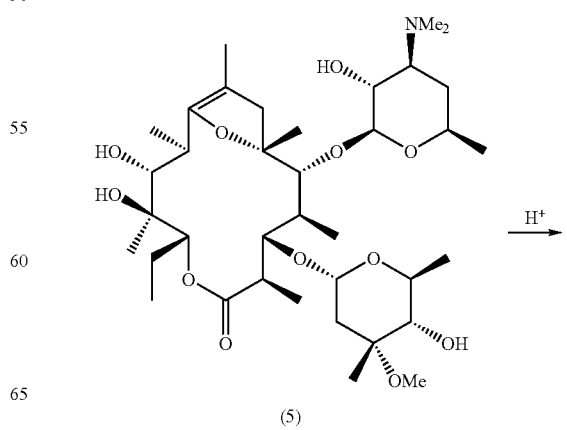

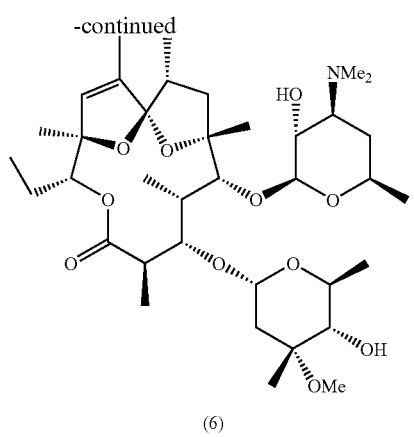

(6)

Spurred by the discovery of motilin agonist activities in compounds (1) and (5), researchers have endeavored to discover new motilides, as macrolides with prokinetic activity are called. Much of the research has centered on generating new erythromycin analogs, either via post-fermentation chemical transformation of a naturally produced erythromycin or via modification (including genetic engineering) of the fermentation process. Illustrative disclosures relating to new motilides based on an erythromycin scaffold include: Omura et al., U.S. Pat. No. 5,008,249 (1991) and U.S. Pat. No. 5,175,150 (1992); Harada et al., U.S. Pat. No. 5,470,961 (1995); Freiberg et al., U.S. Pat. No. 5,523,401 (1996); U.S. Pat. No. 5,523,418 (1996); U.S. Pat. No. 5,538,961 (1996); and U.S. Pat. No. 5,554,605 (1996); Lartey et al., U.S. Pat. No. 5,578,579 (1996); U.S. Pat. No. 5,654,411 (1997); U.S. Pat. No. 5,712,253 (1998); and U.S. Pat. No. 5,834,438 (1998); Koga et al., U.S. Pat. No. 5,658,888 (1997); Miura et al., U.S. Pat. No. 5,959,088 (1998); Premchandran et al., U.S. Pat. No. 5,922,849 (1999); Keyes et al., U.S. Pat. No. 6,084,079 (2000); Ashley et al., US 2002/0025936 A1 (2002); Ashley et al., US 2002/0094962 A1 (2002); Carreras et al., US 2002/0192709 A1 (2002); Santi et al., U.S. Provisional Application 60/407,345; Ito et al., JP 60-218321 (1985) (corresponding Chemical Abstracts abstract no. 104:82047); Santi et al., U.S. patent application Ser. No. 10/648,946, filed Aug. 26, 2003; Omura et al., "Gastrointestinal Motor-Stimulating Activity of Macrolide Antibiotics and the Structure-Activity Relationship," J. Antibiotics 38, 1631-2 (1985); Faghih et al., "Preparation of 9-Deoxo-4"-deoxy-6,9-epoxyerythromycin Lactams 'Motilac-tides': Potent and Orally Active Prokinetic Agents," Biorg. & Med. Chem. Lett., 8, 805-810 (1998); Faghih et al., "Synthesis of 9-Deoxo-4"-deoxy-6,9-epoxyerythromycin Derivatives: Novel and Acid-Stable Motilides," J. Med. Chem., 41, 3402-3408 (1998); and Faghih et al., "Entry into Erythromycin Lactams: Synthesis of Erythromycin A Lactam Enol Ether as a Potential Gastrointestinal Prokinetic Agent," Synlett 751 (July 1998). Other disclosures of interest relating to erythromycin derivatives include Freiberg et al., U.S. Pat. No. 3,681,325 (1972) and Napoletano et al., WO 2004/013153 A2 (2004). The disclosures of the documents cited in this paragraph are incorporated herein by reference.

A number of parameters are relevant to the development of erythromycin analogs as motilides. Firstly, the evolution of the erythromycin scaffold in the natural producing organisms has been driven by antibacterial efficacy and not by prokinetic efficacy. Therefore, considerable room remains for optimization of the structure-activity relationship for motilin receptor agonist activity. Secondly, it is in fact undesirable for a motilide to possess antibacterial activity. The GI tract is host to a large population of bacteria, whose exposure to a motilide having antibacterial activity may induce the development in them of resistance to erythromycin antibiotics. Thus, a motilide desirably has enhanced prokinetic activity engineered in and antibacterial activity engineered out. Thirdly, a drawback commonly found among motilides evaluated to date is their propensity to desensitize the motilide receptor, meaning that, after the initial dose, subsequent doses of a motilide elicit a weaker or no response. Fourthly, stability and bioavailability are concerns—witness the ready degradation of erythromycin A in the stomach and the lack of activity in its secondary degradation product. Thus, there exists a continuing need to develop new motilides, balancing the various different performance requirements.

The present invention provides novel erythromycin analogs useful as prokinetic agents.

BRIEF SUMMARY OF THE INVENTION

One aspect of the present invention provides compounds having the structure of formula I:

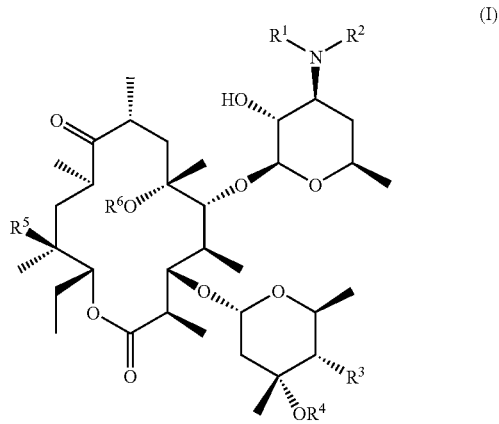

(I)

and the pharmaceutically acceptable salts, esters, and prodrug forms thereof wherein $R^1$, $R^4$, and $R^6$ are independently H or Me;

$R^2$ is substituted or unsubstituted $C_2$-$C_5$ alkyl, alkenyl, or alkynyl; and $R^3$ and $R^5$ are independently H or OH.

Compounds I have unexpectedly been found to possess the desirable combination of good motilin agonist activity and low antibacterial activity, as evidenced by the data provided hereinbelow.

In a second aspect of the invention, the invention provides a method for treating a disorder of gastric motility in a subject suffering from such disorder, comprising administering to a subject in need a therapeutically effective dose of a compound according to formula I.

In a third aspect of the invention, this invention provides a pharmaceutical formulation comprising a compound according to formula (I) and an excipient.

DETAILED DESCRIPTION OF THE INVENTION

Definitions

The definitions of the terms given below apply to the terms as they are used throughout this specification and the appended claims, unless the context clearly indicates otherwise.

"Alkyl" means a straight or branched chain hydrocarbon moiety having the specified number of carbon atoms in the chain or, where the number of carbon atoms is not specified, up to 5 carbon atoms in the chain.

"Alkenyl" means a straight or branched chain hydrocarbon moiety having at least one carbon-carbon double bond and the specified number of carbon atoms in the chain or, where the number of carbon atoms is not specified, up to 5 carbon atoms in the chain.

"Alkynyl" means a straight or branched chain hydrocarbon moiety having at least one carbon-carbon triple bond and the specified number of carbon atoms in the chain or, where the number of carbon atoms is not specified, up to 5 carbon atoms in the chain.

"Alkylaryl," "arylalkyl," "heterocycloalkyl," "alkylheteroaryl," "alkylheterocycle" and the like mean an aryl, heterocyclic, or heteroaryl group, as the case may be, bonded directly to an alkyl moiety, as in benzyl, phenethyl, and the like.

"Aryl" means a monocyclic or bicyclic aromatic hydrocarbon ring system having 6 to 12 carbon atoms in the ring portion, such as phenyl, napthyl, and biphenyl moieties, each of which is optionally substituted at one or more positions.

"Cycloalkyl" means an optionally substituted, saturated cyclic hydrocarbon ring system, preferably containing 1 to 3 rings and 3 to 7 carbons per ring which may be further fused with an unsaturated C3-C7 carbocyclic ring. Exemplary cycloalkyl ring systems include cyclopropyl, cyclobutyl, cyclopentyl, cyclohexyl, cycloheptyl, cyclooctyl, cyclodecyl, cyclododecyl, and adamantyl.

"Halogen" or "halo" means fluorine, chlorine, bromine and iodine.

"Heterocycle", "heterocyclic," or "heterocyclo" means an optionally substituted, fully saturated or unsaturated, aromatic or nonaromatic ring system, for example, which is a 4 to 7 membered monocyclic, 7 to 11 membered bicyclic, or 10 to 15 membered tricyclic ring system, which has at least one heteroatom in at least one carbon atom-containing ring. "Heteroaryl" means a heterocycle in which the ring system is aryl. Each ring of the heterocyclic group containing a heteroatom may have 1, 2 or 3 heteroatoms selected from N, O and S, where the N and S optionally may be oxidized and the N optionally may be quaternized.

Exemplary monocyclic heterocyclic ring systems include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thizaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridinyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like. Preferred heterocyclo groups include pyridinyl, pyrazinyl, pyrimidinyl, pyrroyl, pyrazolyl, imidazolyl, thiazolyl, oxazolyl, isoxazolyl, thiadiazolyl, oxadiazolyl, thienyl, furanyl, quinolinyl, isoquinolinyl, and the like.

"Pharmaceutically acceptable ester" means an ester that hydrolyzes in vivo (for instance in the human body) to produce the parent compound or a salt thereof or has per se activity similar to that of the parent compound. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include formates, acetates, propionates, butyrates, acrylates, citrates, succinates, and ethylsuccinates.

"Pharmaceutically acceptable salt" means a salt of a compound suitable for pharmaceutical formulation. Suitable pharmaceutically acceptable salts include acid addition salts which may, for example, be formed by mixing a solution of a compound with a solution of a pharmaceutically acceptable acid such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where a compound carries one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

Where a group is characterized as being substituted (as in "substituted alkyl," substituted alkenyl," etc.), such group may have one or more independently selected substituents, preferably one to five in number, more preferably one or two in number. It is understood that substituents and substitution patterns can be selected by one of ordinary skill in the art to provide compounds that are chemically stable and that can be synthesized by techniques known in the art as well as the methods set forth herein. Examples of suitable substituents include alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino quarternary ammonium, aralkylamino, cycloalkylamino, heterocycloamino, dialkylamino, alkanoylamino, thio, alkylthio, cycloalkylthio, heterocyclothio, ureido, nitro, cyano, carboxy, carboxyalkyl, carbamyl, alkoxycarbonyl, alkylthiono, arylthiono, alkylsulfonyl, sulfonamindo, aryloxy, and the like, in addition to those specified herein. The substituent may be further substituted, for example, by halo, hydroxy, alkyl, alkoxy; aryl, substituted aryl, substituted alkyl, substituted aralkyl, and the like.

Unless particular stereoisomers are specifically indicated (e.g., by a bolded or dashed bond at a relevant stereocenter in a structural formula), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates are also encompassed within the scope of this invention.

The present invention includes within its scope prodrugs of the compounds of this invention. Such prodrugs are in general functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in Wermuth, "Designing Prodrugs and Bioprecursors," in Wermuth, ed., *The Practice of Medicinal Chemistry*, 2nd Ed., pp. 561-586 (Academic Press 2003).

Compounds and Methods

In a preferred embodiment of the invention, $R^3$ is OH and $R^6$ is H, corresponding to a compound having the structure of formula II

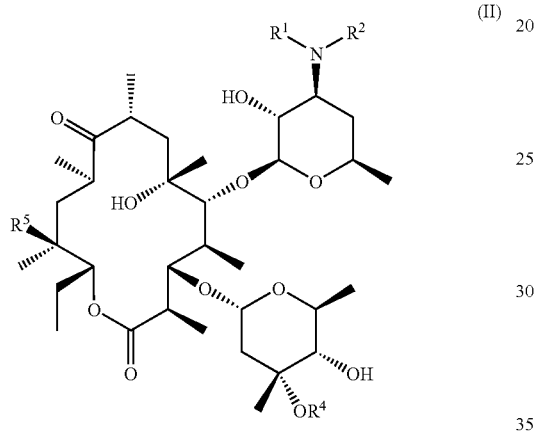

(II)

wherein $R^1$, $R^2$, $R^4$, and $R^5$ are as previously defined.

In another preferred embodiment of the invention, $R^1$ and $R^4$ are Me, $R^3$ is OH, and $R^5$ and $R^6$ are each H, corresponding to a compound having the structure of formula III

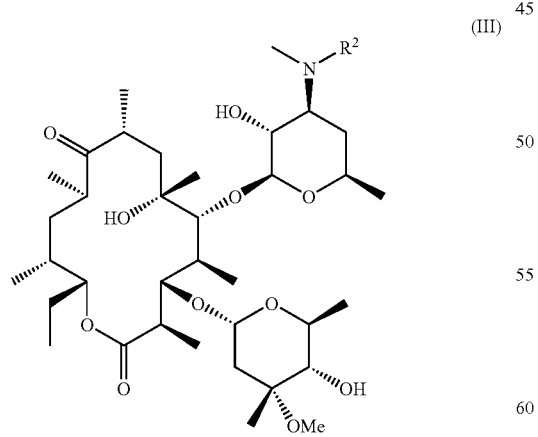

(III)

wherein $R^2$ is as previously defined.

Preferably, $R^1$ is Me. $R^3$ preferably is OH. $R^5$ and $R^6$ are preferably H. Preferably, $R^2$ is an unsubstituted $C_2$-$C_5$ alkyl group, more preferably an unsubstituted $C_3$-$C_4$ alkyl group.

Specific examples of groups $R^2$ include ethyl, isopropyl, n-propyl, n-butyl, isobutyl, 2-butyl, n-pentyl, and isopentyl. Especially preferred groups $R^2$ are isopropyl and isobutyl. The aforementioned preferences are exercised independent of each other.

Specific preferred compounds of this invention include compounds IVa and IVb, whose structures are provided below.

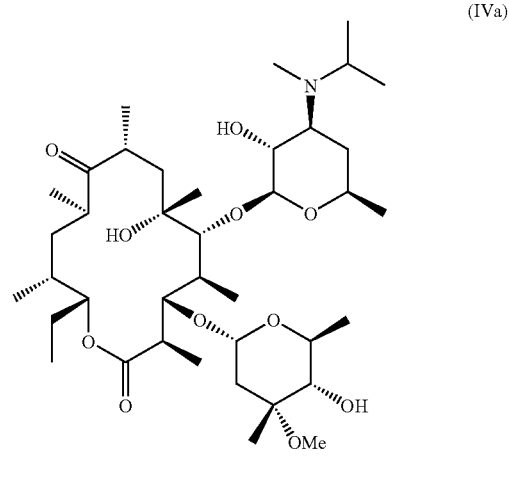

(IVa)

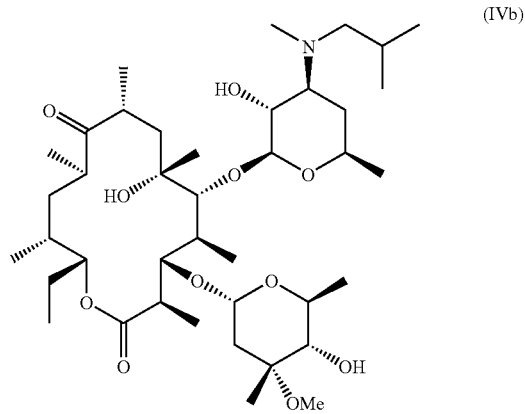

(IVb)

In the semi-systematic nomenclature of erythromycin derivatives employed in the art, compounds I may be generically described as N-desmethyl-N-substituted-11-deoxyerythromycin compounds. Thus, compound IVa may be referred to as N-desmethyl-N-isopropyl-11-deoxyerythromycin B, while compound IVb may be referred to as N-desmethyl-N-isobutyl-11-deoxyerythromycin B.

Compounds of this invention can be synthesized from the corresponding 11-deoxyerythromycin compound 7 by the method shown in Scheme 1 below (illustrated in the context of $R^1$ equals methyl). Demethylation of compound 7 is effected by treatment with iodine in the presence of base, to yield N-desmethyl compound 8. Alkylation of compound 8 with an alkylating agent (X equals halogen or other leaving group) provides compounds I' of this invention (i.e., compounds I in which $R^1$ is Me).

Scheme 1

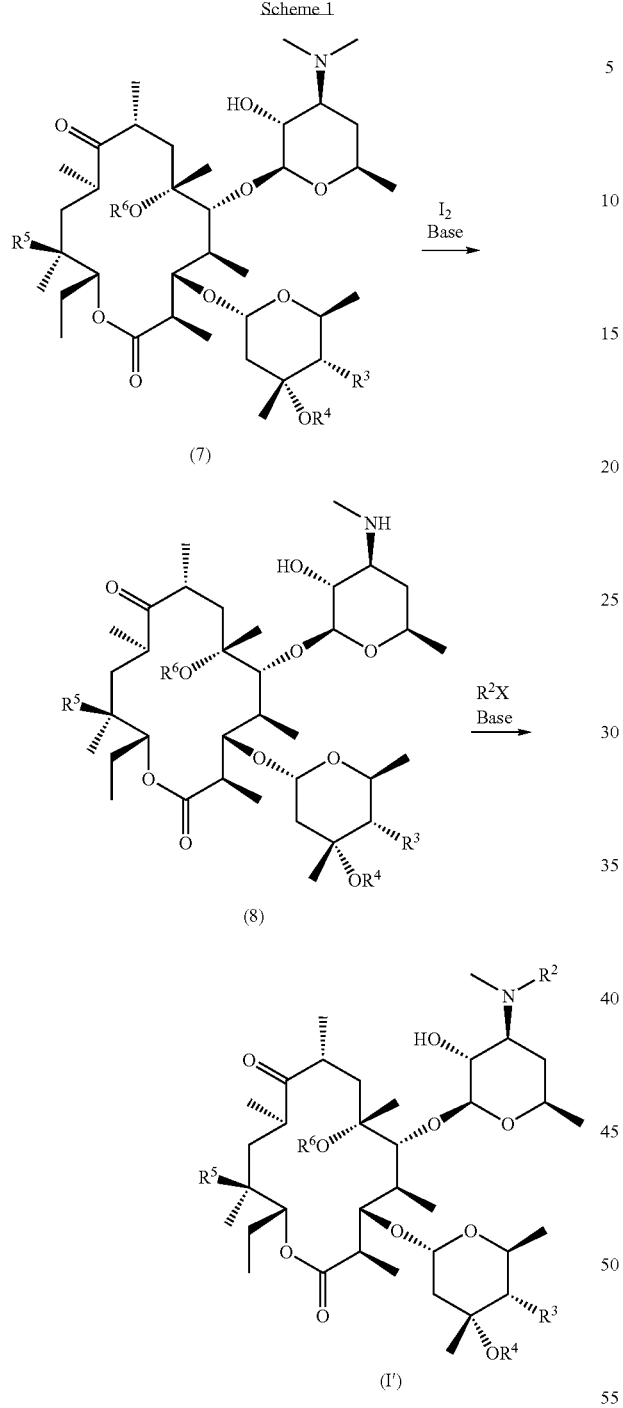

In the instance in which $R^1$ is H, synthesis can be accomplished by either of two alternative routes. In the first route, compound 7 is demethylated twice (the second demethylation using more vigorous conditions) to yield the N-didesmethyl compound (i.e., bearing an amino ($NH_2$) group on the desosamine unit), which is then alkylated once, using one equivalent of an alkylating agent $R^2X$. In the second route, the procedure of Scheme 1 is followed, but compound I' is then demethylated to yield compound I" (i.e., compound I in which $R^1$ is H).

An effective amount of a compound of this invention may be administered as a pharmaceutical formulation in combination with a pharmaceutically acceptable carrier. Treatment may be reactive, for treating an existing condition, or prophylactic, to forestall development of a condition.

The practice of this invention can be further understood by reference to the following examples, which are provided by way of illustration and not of limitation. The synthesis of compounds of this invention is illustrated with particular reference to compounds IVa and IVb. The starting point is 11-deoxyerythromycin B, whose structure is shown below:

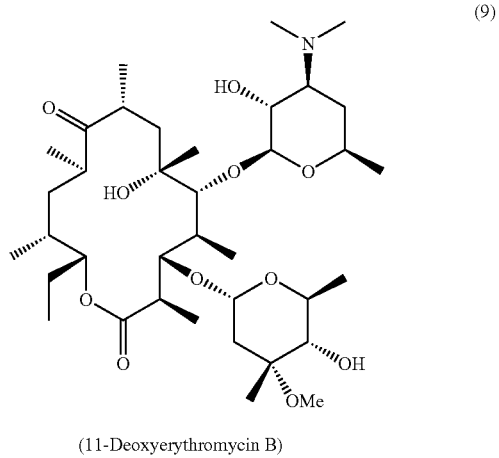

(11-Deoxyerythromycin B)

11-Deoxyerythromycin B can be prepared using genetically engineered microorganisms. The erythromycins are polyketides, synthesized by enzyme systems referred to as polyketide synthases ("PKSs"). The genes encoding PKSs have been extensively studied from the regard of genetic engineering. In one approach, one or more genes encoding a polyketide synthase that in its native form produces 6-deoxyerythronolide B are engineered so as to provide one or more genes encoding a polyketide synthase that produces 6,11-dideoxyerythronolide B, which serves as a precursor to the 11-deoxyerythromycins. Examples of genes encoding suitable polyketide synthases include but are not limited to the eryAI, eryAII, and eryAIII genes from *Saccharopolyspora*

*erythraea*, described in Katz et al., U.S. Pat. No. 5,824,513 (1998); the megAI, megAII, and megAIII genes from *Micromonospora megalomicea*, described in McDaniel et al., U.S. Pat. No. 6,524,841 (2003); the oleAI, oleAII, and oleAIII genes from *Streptomyces antibioticus*, described in Betlach et al., U.S. Pat. No. 6,251,636 (2001); the picA, picB, picC, and picD genes from *Streptomyces venezuelae*, described in Ashley et al., U.S. Pat. No. 6,503,741 (2003); and the narbonolide synthase genes from *Streptomyces narbonensis*, described in Betlach et al., U.S. Pat. No. 6,303,767 (2001), each of which is incorporated herein by reference. In one embodiment, the eryAI gene is engineered by replacement of the ketoreductase domain in module 2 with a cassette containing a dehydratase domain, an enoylreductase domain, and a ketoreductase domain, for example taken from module 1 of the rapamycin PKS. Methods for domain replacement are provided in, for example, McDaniel, U.S. Pat. No. 6,403,775 (2002), which is incorporated herein by reference.

The engineered eryAI gene can be introduced along with the eryAII and eryAIII genes into a host cell competent in the production of polyketides once the engineered PKS genes have been added. Preferably, these host cells are "clean hosts," wherein their native PKS genes have been removed. Examples of suitable host cells for production of 6,11-dideoxyerythronolide B include but are not limited to *Streptomyces coelicolor* CH999, described in Khosla et al., U.S. Pat. No. 5,830,750 (1998); and *Streptomyces lividans* K4-114, described in Ziermann et al., U.S. Pat. No. 6,177,262 (2001), each of which is incorporated herein by reference. Methods for the introduction of PKS genes into host cells are provided in, for example, McDaniel, U.S. Pat. No. 6,403,775 (2002), which is incorporated herein by reference.

The host cell comprising the engineered PKS genes is cultured under conditions wherein 6,11-dideoxyerythronolide B is produced, and the 6,11-dideoxyerythronolide B is isolated, for example by extraction from the broth using organic solvent such as ethyl acetate or dichloromethane, or by solid phase extraction using an absorbent such as XAD-16 resin. Methods for the isolation and purification of these compounds are provided in, for example, McDaniel U.S. Pat. No. 6,403,775 (2002), which is incorporated herein by reference.

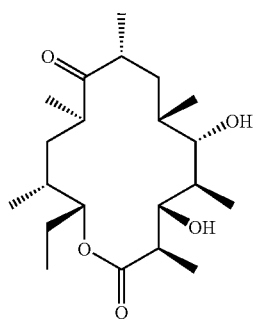

6,11-Dideoxy-erythronolide B (10)

The isolated 6,11-dideoxyerythronolide B is converted to 11-deoxyery-thromycins using a culture of a converter strain competent in production and addition of the glycosyl units and in hydroxylation of the 6- and 12-carbons of erythronolides, but incompetent in the production of erythromycins due to the absence of a functional polyketide synthase. Such converter strains may be mutants expressing defective polyketide synthases, or may be clean hosts wherein the polyketide synthase genes have been removed. Preferably, the converter strain is the clean host *Saccharopolyspora erythraea* K24-1, described in Santi et al., US 2002/0004229 A1 (2002), incorporated herein by reference. Methods for the conversion of erythronolides into erythromycins are provided in, for example, Chu et al., U.S. Pat. No. 6,451,768 (2002), which is incorporated herein by reference. *Saccharopolyspora erythraea* K24-1 was deposited with the American Type Culture Collection, P.O. Box 1549, Manassas, Va. 20108, USA, according to the terms of the Budapest Treaty on Mar. 12, 2003, under accession number PTA-5061. Conversion methodology is further described in Carreras et al., *J. Biotechnol.*, 92 (2002) 217-228, "*Saccharopolyspora erythraea*-catalyzed bioconversion of 6-deoxyerythronolide B analogs for production of novel erythromycins," the disclosure of which is incorporated herein by reference.

Alternatively, 11-deoxyerythromycin B can be prepared in a single fermentation. In this embodiment, the engineered eryAI gene is incorporated along with the eryAII and eryAIII genes into a host cell competent in the production of erythromycins once the engineered PKS genes have been added. In preferred embodiments, these host cells are "clean hosts," wherein their native PKS genes have been removed. Examples of suitable hosts include but are not limited to the clean host *Saccharopolyspora erythraea* K24-1 and strains of *Saccharopolyspora erythraea* having mutated PKS genes such as those described in Santi et al., US 2002/0004229 A1 (2002), which is incorporated herein by reference. Strain K24-1 has had the native eryAI, eryAII, and eryAIII genes replaced with the attB phage attachment site of the actinophage ΦC31, described in U.S. Pat. No. 5,190,871, incorporated herein by reference, and followed by the ermE* promoter. This allows plasmid vectors comprising the complementary attP phage attachment site along with the genes to be delivered to integrate into the chromosome at the attB site in the presence of a phage integrase. Examples of suitable integrating phage vectors include but are not limited to pSET152 and its derivatives.

Compounds (I) of this invention can also be used for the preparation of a medicament for treating a gastric motility disorder in a subject.

Compounds (I) of this invention can be administered in a dosage in the range of 1 to 5 mg/kg. Administration can be intravenous or orally. Where administered orally, the amount administered preferably is higher than that used for intravenous administration, by a factor of two or three.

Compounds of this invention may be used in a pharmaceutical formulation comprising a compound of this invention and an excipient. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy*, 20th Ed. (Lippincott Williams & Wilkins 2003), the disclosure of which is incorporated herein by reference.

The practice of this invention can be further understood by reference to the following examples, which are provided by way of illustration and not of limitation.

EXAMPLE 1

*Saccharopolyspora erythraea* K24-1/159-44

This example describes the construction of a strain of *Saccharopolyspora erythraea* (K24-1/159-44) capable of the biosynthesis of 11-deoxyerythromycins in a single fermentation.

Preparation of starting host strain *Saccharopolyspora erythraea* K24-1 is described in Santi et al., US 2002/0004229 A1 (2002), and the strain was deposited with the American Type Culture Collection, P.O. Box 1549, Manassas, Va. 20108, USA, according to the terms of the Budapest Treaty on Mar. 12, 2003, with accession number PTA-5061.

pKOS159-8 and pKOS159-10 are derivatives of pSET152 containing the eryA genes under the control of the ermEp* promoter and the actIp/actII-ORF4 promoter-activator pair, respectively. A 35 kb NsiI fragment from pKAO127 carrying the eryA genes and the actIp/actII-ORF4 region was cloned into pKOS97-64c (a pSET152 derivative containing the ermEp* promoter and a λ cos site) to make pKOS159-10. The fd transcriptional terminator from the pKAO127 fragment prevents expression of any genes from the ermEp* promoter in this plasmid. The fragment containing the fd terminator and actIp/actII-ORF4 segment in pKOS159-10 was removed by digestion with PacI and self-ligation to generate pKOS159-8. For expression of eryA genes under their natural promoter, pKOS159-31 was constructed by cloning the NdeI-XbaI fragment carrying the eryA genes (and λ cos site) from pKOS159-10 and the XbaI-NdeI digested PCR amplified eryAI left flank fragment from above into pSET152 digested with XbaI. pKOS159-33, which contains the eryA genes from *S. erythraea* K41-135 was constructed in an analogous way using the eryA fragment from pKOS108-04. Likewise, all engineered DEBS expression plasmids were made using pKOS159-31 as a scaffold and appropriate restriction enzymes to move the genetically modified eryA fragment from existing plasmids.

pKOS159-44 is a pSET152 (Bierman et al., *Gene* 116, 43-49 (1992), "Plasmid cloning vectors for the conjugal transfer of DNA from *Escherichia coli* to *Streptomyces* spp.") derivative plasmid that has genetically modified eryA genes (KR2→rapDH/ER/KR1) under the control of eryAI promoter (Rodriguez et al., "Rapid Engineering of Polyketide Overproduction by Gene Transfer to Industrially Optimized Strains," *J. Ind. Microbio. Biotechnol.*, 8, 480-8 (2003)). A 30 kb NdeI-NsiI fragment (carrying genetically modified eryA genes) from pKOS11-66 (Xue et al., *Proc. Natl. Acad. Sci. U.S.A.*, 96, 11740-11745 (1999), "A multiplasmid approach to preparing large libraries of polyketides") was isolated and ligated to a 8 kb NdeI-NsiI fragment from pKOS159-33 (Rodriguez et al., cited supra), containing the vector pSET152, eryAp promoter and cos λ site). The ligation mixture was packaged using Gigapack III Gold packaging extract (Stratagene), and used to infect *E. coli* XL-1 Blue. Recombinats were selected on LB agar plates containing 60 µg/ml apramycin. pKOS159-44 plasmid DNA was isolated and checked by restriction digestions.

*S. erythraea* strain K24-1, which contains a chromosomal deletion of the three eryA genes and insertion of the attB loci for the *Streptomyces* phage φC31 from *Streptomyces lividans*, followed by the ermE* promoter in their place, was prepared by harvesting spores from strains grown on 1-2 M1 plates (per liter, 5 g glucose, 5 g tryptone, 0.5 g betaine hydrochoride, 5 g corn starch, 1 g corn steep liquor (50%), 200 mg $MgSO_4.7H_2O$, 2 mg $ZnSO_4.7H_2O$, 0.8 mg $CuSO_4.5H_2O$, 0.2 mg $CoCl_2.6H_2O$, 4 mg $FeSO_4.7H_2O$, 80 mg $CaCl_2.6H_2O$, 150 mg $KH_2PO_4$, 10 g NaCl, 20 g agar) filtering the spores through sterile cotton, and resuspending in 1 ml of 20% glycerol. Spore suspensions were stored at −20° C. A 20 µL aliquot of the spore suspension was added to 5 mL of 2×YT and incubated at 30° C. with shaking. After 1 h the spores were collected by centrifugation (recipient cells). Donor cells were prepared by transforming *E. coli* ET12567/pUZ8002 with pKOS159-44 and selecting for apramycin resistance only. Several colonies were picked off the primary transformation plate and used to inoculate 5 ml of LB with chloramphenicol (10 µg/mL) kanamycin (100 µg/mL) and apramycin (60 µg/mL). The cells were grown at 37° C. for 3-4 h ($OD_{600}$ of 0.4-0.6), collected by centrifugation, washed in 5 mL LB, centrifuged, and resuspended in 100 µL of LB. Conjugal transfer between the donor and recipient cells was performed by resuspending the recipient cells in the 100 µl donor suspension and the cells were spread on R5 plates (Hopwood et al., *Genetic Manipulation of Streptomyces: A Laboratory Manual* (The John Innes Foundation, Norwich, UK, 1985) containing 50 µg/mL nalidixic acid and incubated at 34° C. for 16 h. The plates were then overlayed with 3 mL of soft nutrient agar containing 1 mg nalidixic acid and 2 mg apramycin. Exconjugants K24-1/159-44 were observed after 48 h of further incubation.

Strain K24-1/159-44 was deposited with the American Type Culture Collection, P.O. Box 1549, Manassas, Va. 20108, USA, according to the terms of the Budapest Treaty on Mar. 12, 2003, with accession number PTA-5054.

EXAMPLE 2

11-Deoxyerythromycin B (9)

This example describes the preparation of 11-deoxyerythromycin B (9), using strain K21-1/159-44, described in the previous example, as the producing strain. Fermentation techniques disclosed in Frykman et al., *Biotechnol. Bioeng.*, 76, 303-310 (2001) "Precursor-Directed Production of Erythromycin Analogs by *Saccharopolyspora erythraea*," and Rodriguez et al., cited supra, the disclosures of which are incorporated by reference, were followed.

The following media were used: (a) Seed medium V1 contained 16 g/L corn starch, 10 g/L dextrin (D-2256, Sigma-Aldrich), 15 g/L soybean flour (S-9633, Sigma-Aldrich), 2.5 g/L sodium chloride, 5 g/L corn steep liquor, 1 g/L ammonium sulfate (A-2939, Sigma-Aldrich), 6 g/L soybean oil (S-7381, Sigma-Aldrich), and 4 g/L calcium carbonate (C-4830, Sigma Aldrich). (b) Fermentation medium F2 contained 28 g/L corn starch, 24 g/L soybean meal, 5.5 g/L sodium chloride, 8 g/L corn steep liquor, and 1.5 g/L ammonium sulfate, 4.5 g/L soybean oil, and 6 g/L calcium carbonate. All media were sterilized by autoclaving at 121° C. for 90 min.

Two seed flasks were started by taking a 1 mL vial of *Saccharopolyspora erythraea* K24-1/pKOS159-44 from a frozen cell bank, thawing, and adding the vial contents into 50 mL of medium V1 and incubating at 34° C. for 40-48 h. Two secondary seeds were then created by transferring 50 mL aliquots from the seed flask to 500 mL of medium V1 and incubating at 34° C. for 40-48 h.

Both 500 mL secondary seed cultures were transferred to a B. Braun B10 fermenter containing 9 L of medium V1. The fermenter was operated at 34° C. and maintained at pH 7.0 by addition of 2.5 N sulfuric acid and 2.5 N sodium hydroxide. Aeration at 3 LPM and agitation at 600 to 800 rpm were provided, maintaining the dissolved oxygen tension at greater than 40%. Harvesting took place after about 24 h.

15

Then, 10 L of the fermenter seed culture was transferred to a B. Braun Biostat UD500 fermenter containing 300 L medium F2. The Biostat UD500 fermenter was operated at 34° C. and maintained at pH 7.0 by the addition of 2.5 N sulfuric acid and 2.5 N sodium hydroxide. Agitation at 200-300 rpm and aeration at 40-250 LPM were provided, maintaining the dissolved oxygen tension at greater than 40%. Dextrin (150 g/L) was fed at a rate of 675 mL/h from 24 to 98 h. Soybean oil was fed at a rate of 64 mL/h from 24 to 140 h. n-Propanol was fed at a rate of 26 mL/h from 24 to 140 h. Harvesting took place after 180 h.

Foaming was controlled by the addition of a 50% solution of antifoam B (JT Baker) as needed.

The fermentation broth was clarified by centrifugation and was subjected to solid phase extraction using HP20 resin (Mitsubishi). Adsorbed product was eluted with methanol and dried. The crude product was then subjected to ethyl acetate:water liquid:liquid extraction. The combined ethyl acetate extracts were dried. The product was purified by chromatography using HP20SS resin, eluting with a step-gradient from 50% to 80% methanol. The product containing fractions were pooled and dried, to provide 11-deoxyerythromycin B. m/z: 702.64 (MH); $^{13}$C-NMR (CDCl$_3$): 219.13, 175.56, 102.48, 95.92, 82.73, 79.40, 78.92, 77.79, 74.88, 72.52, 70.79, 68.80, 65.52, 65.13, 49.25, 45.98, 44.31, 43.40, 40.15 (2×), 38.11, 37.20, 36.54, 34.79, 33.19, 28.52, 26.37, 24.55, 21.37, 21.19, 18.54, 18.31, 15.69, 14.68, 11.96, 10.36, 9.16 ppm.

EXAMPLE 3

N-Desmethyl-11-deoxyerythromycin B (11)

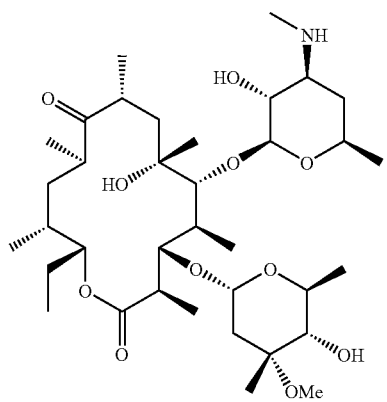

(11)

A mixture of 11-deoxyerythromycin B (9, 200 mg, 0.285 mmol) and sodium acetate (117 mg, 1.43 mmol) in methanol-water (8:2 V/V, 15 mL) was stirred at 50° C., iodine (72.5 mg, 0.285 mmol) was then added. During the reaction 1N sodium hydroxide (0.29 mL) was added in small portions. Completion of the reaction after 1 h was confirmed by thin-layer chromatographic analysis. After removal of solvent, the mixture was extracted three times with ethyl acetate and dried over sodium sulfate. Crude compound 11 (170 mg) was obtained as a white solid, which was used for next step without further purification. m/z: 688.5 (MH).

16

EXAMPLE 4

N-Desmethyl-N-isopropyl-11-deoxyerythromycin B
(IVa)

A mixture of N-desmethyl-11-deoxyerythromycin B (described above, 60 mg, 0.087 mmol), diisopropylethylamine (113 mg, 10 equiv), 2-iodopropane (299 mg, 20 equiv) in acetonitrile (4 mL) was stirred in a 70° C. bath overnight. Water and saturated sodium bicarbonate were added and the solution was extracted three times with ethyl acetate and dried over magnesium sulfate. The crude product was purified on a silica gel column (3:1 hexane-acetone, 1% triethylamine) to give pure compound IVa (35 mg, 48% yield for 2 steps).). m/z: 730.5 (MH); $^{13}$C-NMR (CDCl$_3$): 219.23, 175.74, 102.45, 95.88, 82.54, 79.40, 79.05, 77.90, 75.01, 72.62, 70.30, 68.90, 65.63, 62.41, 52.48, 49.32, 44.32, 43.52, 40.35, 38.13, 37.58, 36.61, 34.86, 33.29, 29.58, 29.16, 26.41, 24.63, 21.46, 21.28, 20.98, 20.35, 18.60, 18.35, 15.73, 14.65, 11.95, 10.42, 9.14 ppm.

EXAMPLE 5

N-Desmethyl-N-isobutyl-11-deoxyerythromycin B
(IVb)

A mixture of N-desmethyl-11-deoxyerythromycin B (described above, 30 mg, 0.044 mmol), diisopropylethylamine (56.4 mg, 10 equiv), 1-iodo-2-methylpropane (160 mg, 20 equiv) in acetonitrile (2 mL) was stirred in a 65° C. bath for 20 h. Water and saturated sodium bicarbonate were added and the solution was extracted three times with ethyl acetate and dried over magnesium sulfate. The crude product was purified on a silica gel column (3:1 hexane-acetone, 1% triethylamine) to give pure compound IVb (15 mg, 40% yield for 2 steps). m/z: 744.5 (MH); $^{13}$C-NMR (CDCl$_3$): 219.28, 175.79, 102.46, 95.89, 82.46, 79.32, 79.08, 77.93, 75.11, 72.65, 70.64, 69.07, 66.06, 65.67, 61.35, 49.34, 44.36, 43.51, 40.79, 38.18, 37.18, 36.63, 34.88, 33.29, 29.59, 29.35, 26.47, 26.05, 24.61, 21.51, 21.28, 20.58, 20.35, 18.60, 18.39, 15.76, 14.64, 12.10, 10.45, 9.17 ppm.

EXAMPLE 6

Motilin Agonist Activity

Compounds of this invention were tested for motilin agonist activity, following the procedure of Carreras et al., *Anal. Biochem.*, 300, 146-151 (2002), the disclosure of which is incorporated herein by reference. Table 1 shows the EC$_{50}$ values for activation of the motilin receptor.

TABLE 1

| Motilin Agonist Activity | |
| --- | --- |
| Compound | Motilin Agonist EC$_{50}$ (nM) |
| IVa | 700 |
| IVb | 2,100 |
| Erythromycin A (comparative) | 2,000 |
| 11-Deoxyerythromycin B (comparative) | 1,200 |

EXAMPLE 7

Antibacterial Activity

Compounds of this invention were tested for in vitro activity against three erythromycin sensitive strains of *Streptococcus pneumoniae* (ATCC 6301, ATCC 700671, and ATCC 49619), using methods known in the microbiological art. The results are provided in Table 2:

TABLE 2

| | Antibacterial Activity | | |
| --- | --- | --- | --- |
| | MIC (μg/mL) | | |
| Compound | ATCC 6301 | ATCC 70071 | ATCC 49619 |
| IVa | 12.5 | 200 | 6.25 |
| IVb | 200 | >200 | 200 |
| Erythromycin A | 0.025 | 0.049 | 0.049 |
| 11-Deoxyerythromycin B | 0.049 | 0.78 | 0.098 |

The results of Tables 1 and 2 combine to show that the compounds of this invention possess the desirable juxtaposition of high motilin agonist activity and low antibacterial activity. These results are unexpected, as the structurally similar 11-deoxyerythromycin B, although possessing motilin agonist activity, also possesses high antibacterial potency, comparable to that of the antibiotic erythromycin A.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

We claim:

1. A method of treating a disorder of gastric motility in a subject suffering from such disorder, comprising administering to the subject a therapeutically effective dose of a compound having the structure of IVa:

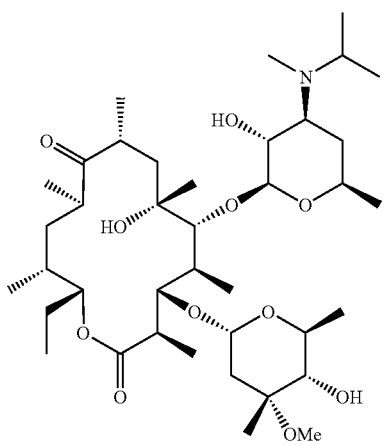

(IVa)

or a pharmaceutically acceptable salt or ester thereof.

2. A method of treating a disorder of gastric motility in a subject suffering from such disorder, comprising administering to the subject a therapeutically effective dose of a compound having the structure of IVb

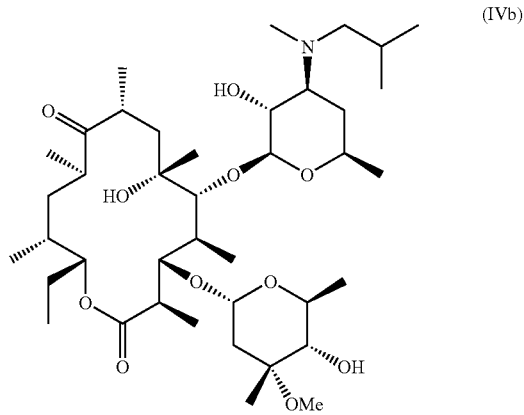

(IVb)

or a pharmaceutically acceptable salt or ester thereof.

3. A pharmaceutical composition comprising a compound having the structure of formula IVa

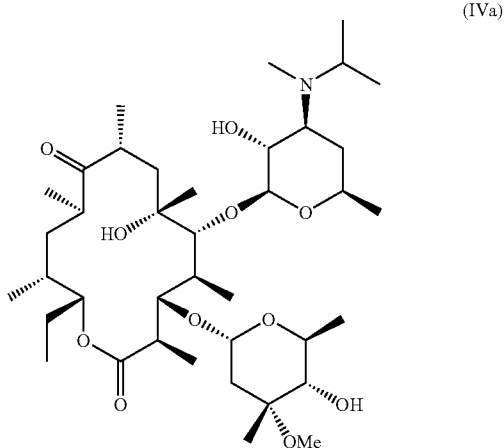

(IVa)

or a pharmaceutically acceptable salt or ester thereof.

4. A pharmaceutical composition comprising a compound having the structure of formula IVb

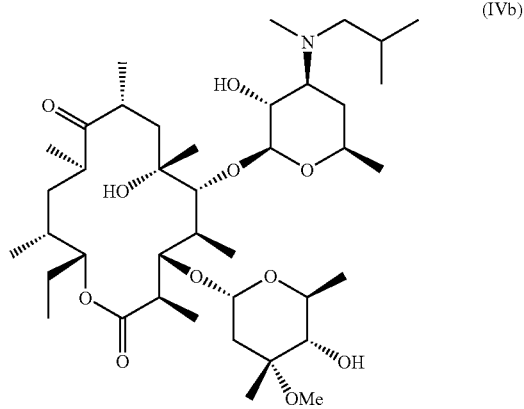

(IVb)

or a pharmaceutically acceptable salt or ester thereof.

* * * * *